(12) United States Patent
Sampson

(10) Patent No.: US 8,282,892 B2
(45) Date of Patent: Oct. 9, 2012

(54) BIO-WASTE STERILIZER

(75) Inventor: Donald L. Sampson, Spokane, WA (US)

(73) Assignee: Globe-Tek LLC, Spokane, WA (US)

( * ) Notice: Subject to any disclaimer, the term of this patent is extended or adjusted under 35 U.S.C. 154(b) by 1051 days.

(21) Appl. No.: 12/236,061

(22) Filed: Sep. 23, 2008

(65) Prior Publication Data

US 2009/0123339 A1 May 14, 2009

Related U.S. Application Data

(60) Provisional application No. 60/988,058, filed on Nov. 14, 2007, provisional application No. 60/988,064, filed on Nov. 14, 2007.

(51) Int. Cl.
| | |
|---|---|
| *A61L 2/08* | (2006.01) |
| *A61L 2/00* | (2006.01) |
| *G21F 9/00* | (2006.01) |
| *B09B 3/00* | (2006.01) |
| *B08B 3/00* | (2006.01) |
| *F26B 25/00* | (2006.01) |
| *F26B 3/34* | (2006.01) |

(52) U.S. Cl. ........ 422/295; 422/297; 422/298; 422/299; 422/300; 422/304; 422/308; 588/1; 588/900; 261/75; 261/DIG. 65; 261/DIG. 76; 134/56 R; 134/84; 134/113; 34/102; 34/524; 34/245

(58) Field of Classification Search ............... 422/26, 422/28, 295, 297–300, 304, 308; 588/1, 588/900; 261/75, DIG. 65, DIG. 76; 134/56 R, 134/84, 113; 34/102, 524, 245
See application file for complete search history.

(56) References Cited

U.S. PATENT DOCUMENTS

| | | | |
|---|---|---|---|
| 5,064,124 A | 11/1991 | Chang | |
| 5,270,000 A * | 12/1993 | Goldner et al. | 422/21 |
| 5,277,136 A | 1/1994 | Davis | |
| 5,364,589 A | 11/1994 | Buehler | |
| 5,398,347 A | 3/1995 | Hall | |
| 5,520,888 A | 5/1996 | Berndt | |
| 5,620,654 A | 4/1997 | Mosenson | |
| 5,799,833 A | 9/1998 | Lewis | |
| 5,799,883 A | 9/1998 | Lewis | |
| 6,357,682 B1 | 3/2002 | Hext | |
| 7,931,860 B1 * | 4/2011 | Lewis et al. | 422/26 |

FOREIGN PATENT DOCUMENTS

| | | |
|---|---|---|
| EP | 0400676 | 5/1990 |
| EP | 0400676 | 12/1990 |

\* cited by examiner

*Primary Examiner* — Jill Warden
*Assistant Examiner* — Monzer Chorbaji
(74) *Attorney, Agent, or Firm* — Farrell Patent Law PC; Mark Farrell

(57) ABSTRACT

Bio-waste sterilizers are described. In one implementation an exemplary system has waste transport vessels that can be intermittently heated and pressurized, for example, with steam, and are interconnected to provide multiple sterilization pathways for waste as the waste is transported. Selected sterilization pathways may depend on attributes of the waste. Sterilization factors, such as mechanical shredding, application of steam, application of pressure, maintenance of temperature, separation of liquid, etc., are integrated into the waste transport features of the system, which can be made compact to save space while processing relatively large bulk amounts of materials, such as medical wastes. The system maintains safe isolation of bio-hazardous components in the waste from the external environment. A system controller provides parameters management, smart sterilization cycle control, quality assurance, safety management, diagnostics, and reporting over a network.

11 Claims, 5 Drawing Sheets

BIO-WASTE STERILIZER

RELATED APPLICATIONS

This patent application claims priority to U.S. Provisional Patent Application No. 60/988,058 to Sampson, entitled, "Bio-Waste Sterilizer," filed Nov. 14, 2007, and to U.S. Provisional Patent Application No. 60/988,064 to Sampson, entitled, "Bio-Waste Sterilizer," filed Nov. 14, 2007, both incorporated herein by reference.

TECHNICAL FIELD

The subject matter presented herein relates generally to medical waste decontamination and environmental safety, and more particularly to bio-waste sterilizers.

BACKGROUND

Tons of biohazardous waste are generated daily by hospitals, veterinary facilities, universities, and government agencies. Conventional autoclaves and sterilization techniques attempt to disinfect or sterilize the bio-waste but have several significant shortcomings. Either the waste does not get completely sterilized or an undue amount of handling and energy is used to effect satisfactory sterilization. Also, conventional equipment for sterilizing bio-waste often requires intensive human intervention to handle the bio-waste or to initiate the various decontamination steps to be performed by a conventional machine. Conventional bio-waste sanitation equipment also tends to be cumbersome and occupy a significant amount of floor-space or ground-space, an undesirable characteristic in many compact settings, such as private clinics, airport concessions, cruise ships, and military deployments.

SUMMARY

Bio-waste sterilizers are described. In one implementation an exemplary system has waste transport vessels that can be intermittently heated and pressurized, for example, with steam, and are interconnected to provide multiple sterilization pathways for waste as the waste is transported. Selected sterilization pathways may depend on attributes of the waste. Sterilization factors, such as mechanical shredding, application of steam, application of pressure, maintenance of temperature, separation of liquid, etc., are integrated into the waste transport features of the system, which can be made compact to save space while processing relatively large bulk amounts of materials, such as medical wastes. The system maintains safe isolation of bio-hazardous components in the waste from the external environment. A system controller provides parameters management, smart sterilization cycle control, quality assurance, safety management, diagnostics, and reporting over a network.

This summary section is not intended to give a full description of the portable worker safety frame, or to provide a list of features and elements. A detailed description of example embodiments of the portable worker safety frame follows.

DETAILED DESCRIPTION

Overview

Figure 1:
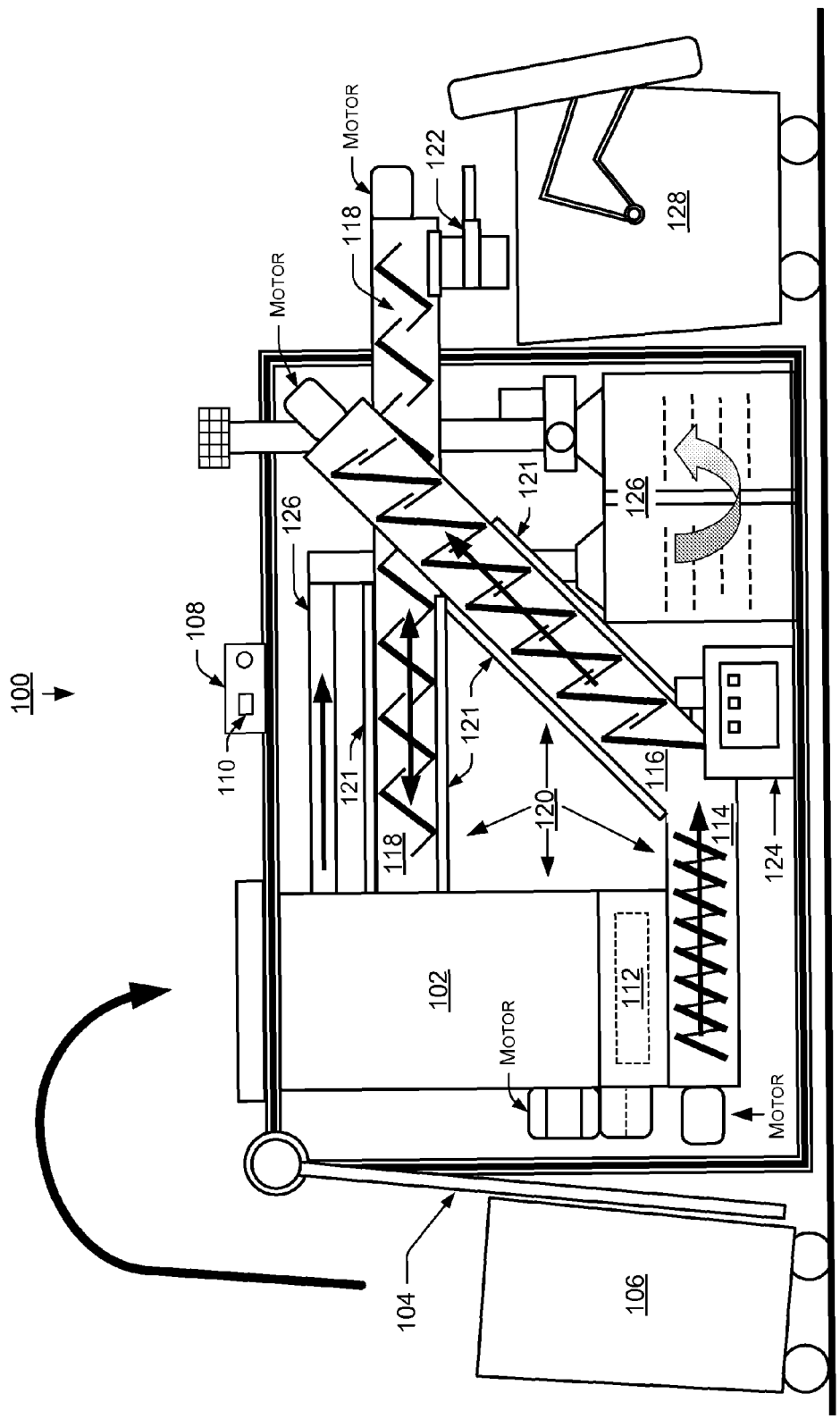
FIG. 1 is diagram of a first exemplary implementation of a bio-waste sterilizer.

This disclosure describes bio-waste sterilizer systems and methods. Exemplary bio-waste sterilizers described herein provide reliable sterilization of bio-wastes, such as potentially infectious medical wastes (hereinafter, "wastes") generated by hospitals, while reducing the amount of human intervention needed to process the wastes. Exemplary bio-waste sterilizers are relatively compact in relation to the capacity of waste they can handle, compared with conventional machines that sanitize such wastes. The relative compactness reduces the footprint and space needed for equipment to sterilize a given amount of waste, compared with conventional sanitizers.

The exemplary bio-waste sterilizers have safety features to protect workers and the environment. Likewise, the bio-waste sterilizers are robust to abnormalities, such as power outages, and in one implementation can self-diagnose problems in order to either self-correct or provide troubleshooting data.

An exemplary controller included in each bio-waste sterilizer directs operations and can modify sterilization cycles according to the type of waste specified by an operator or according to local regulatory standards for waste sterilization. The controller can interface with local and remote computers via phone or network to provide real-time status of operations, statistics, verification that sterilization benchmarks have been met, and other relevant data. Exemplary bio-waste sterilizers can also generate, transmit, and store an electronic record of sterilization cycle activity, system set points, diagnostic data, and other information that can be displayed on a readout or transmitted to a remote location via a network, such as the Internet.

The bio-waste sterilizer includes many advantageous features. In one implementation, the bio-waste sterilizer includes shredding and re-shredding steps to increase the surface area of waste immediately exposed to steam and/or a high temperature and pressure. Sterilization occurs during transport and tumbling of the shredded waste, further increasing immediate exposure of the waste to the sterilizing action. The exemplary controller ensures that the waste is thoroughly exposed to steam, heat, pressure, etc., for a sufficient time interval for sterilization to occur. Parameters are programmable to satisfy local jurisdictional standards for processing waste. If there is any deviation, because of power outage, etc., the controller resets the sterilization cycle to appropriate set points to finish the sterilization operation successfully.

First Exemplary Bio-Waste Sterilization System

In its many implementations, the exemplary bio-waste sterilizer aims to provide rapid and superior sterilization using equipment that occupies a small footprint and is adaptable to relatively small work areas. Some implementations of the bio-waste sterilizer are appropriate for such applications as airport concessions, private clinics, cruise ship waste disposal, and military deployments. Other implementations of the bio-waste sterilizer have a capacity to handle a higher waste treatment rate. For example, various implementations may process 220 pounds per hour, 660 pounds per hour, or 1100 pounds per hour.

FIG. 1 shows an exemplary bio-waste sterilizer 100 for handling approximately between 220-660 pounds of waste per hour. The waste to be sterilized is placed inside a feed hopper 102 either manually or, in one implementation, by using an optional semi-automatic feed system 104. The waste is typically brought for treatment in re-useable containers 106. Once the waste has been placed into the bio-waste sterilizer 100, a door to the feed hopper 102 can be closed and locked, and the sterilization process can be started by an operator through an automatic control system that includes an exemplary controller 110. The first waste that is placed into the feed hopper 102 falls by gravity or is pushed by a mechanism into a shredder 112 and then conveyed into treatment screws 114, 116, and 118 to be exposed to sterilizing action. Once the first waste material is shredded, the operator can select to refill the feed hopper 102 multiple times, e.g., an additional two times, to fill the entire volume of components that constitute a pressure vessel ("treatment vessel" 120), before starting the sterilization cycle.

In the illustrated implementation, the pressurized treatment vessel 120 is made up of the feed hopper 102, the shredder 112, and the treatment screws 114, 116, and 118. The treatment screws 114, 116, and 118 each consist, in one implementation, of a screw conveyor with worm drive transport action, enclosed in a cylinder in order to transport the waste by the conveyance action of the screw blade or other internal element. Each screw element of each treatment screw 114, 116, 118 may have metal or carbide edges that are sharpened, hardened, serrated, etc. to improve durability and assist in breaking apart the waste. Each cylinder may be surrounded in whole or in part by a heating jacket 121.

Each heating jacket 121 produces heat by including electric heating coils or by having a fluid space for the flow of heated oil. The heat imparted by the heating jackets 121 is regulated by the controller 110 and is typically an integral element of the sterilization action, e.g., when applied along with steam and pressure for an adequate time interval.

In one implementation, no shredding of the waste occurs until a lid or door of the feed hopper 102 is shut and locked. Once the lid is shut and locked, the waste material can be fed onto a heavy duty implementation of the shredder 112 by gravity and is pulled into the cutting action of the shredder 112, e.g., by opposing rotation of a dual shafted design.

The shredding of the waste material and associated size reduction of waste components opens most small hollow voids and spaces in the various waste items ensuring adequate steam exposure during the sterilization process. Waste with ill-fitting geometry such as syringes, cannulas, tubing, cutlery, etc., can be reduced to a mean edge length of approximately 20×30 mm. The shredder 112 can reduce the waste volume by approximately 80%.

A blocking isolation valve 122 mounted at a discharge of the treatment vessel 120 is closed during the sterilization cycle thereby isolating the waste material from the atmosphere.

Once the bio-waste sterilizer 100 is filled with waste material, the sterilization cycle begins. Saturated steam is injected into the treatment vessel by a built in steam generator 124. The controller 110 automatically and accurately controls the temperature and pressure of the sterilization process. The controller 110 can be a programmable logic controller-based (PLC-based) system, and is described in greater detail below, in association with FIG. 4.

During the sterilization cycle, the waste material is continually tumbled and conveyed through the treatment screws 114, 116, 118 and in one implementation, recycled back through the shredder 112.

Temperature, pressure, and exposure time are adjustable via the controller 110 and can be preset per local regulations. During the sterilization process, the waste is continually tumbled while conveyed, and thus exposed to sterilization action by the screw motion of the contained treatment screws 114, 116, and 118, ensuring that all of the waste is fully exposed to the steam and heat of the sterilization process.

After completion of the sterilization cycle, the steam is vented from the treatment vessel 120, the blocking isolation valve 122 is opened, and the rotational action of the treatment screw 118 is reversed, rendering the treatment screw 118 into a discharge transport screw, conveying the sterilized waste material through a discharge opening or tube for appropriate customer disposal 128.

During the loading process, the entire feed system or feed hopper 102 is held continually under negative air pressure or vacuum by a built in air filtration system 126. The air being pumped out to create the negative pressure is processed through a state-of-the-art three-stage air filtration system that in one implementation includes an activated charcoal stage; an aluminum oxide ceramics stage; and a HEPA filter(s) stage.

In one implementation, the above-described bio-waste sterilizer 100 has a waste treatment rate of approximately 220-600 pounds per hour, when the bulk weight of the waste is approximately 8 pounds per cubic foot. The volume of the feed hopper 102 is approximately 60-200 gallons. The shredder 112 is powered by a motor that may be approximately 10-25 horsepower. In one implementation, the heating jacket 121 preferably uses electric heating with a waste pre-heating output of approximately 20-40 kW. The waste treatment temperature is approximately 284° Fahrenheit. The steam set-output is approximately 5-20 kW. For the air filtration system 126, a 1.5-3.0 horsepower blower motor may be used. To implement a negative air pressure, air is drawn off from the feed hopper 102 at a rate of approximately 800-2300 cubic feet per minute, and subjected to HEPA filtration. In one implementation, the bio-waste sterilizer 100 & 200 is connected to a 440 volt, 60 hertz, 3-phase power source and consumes approximately between 40-150 kW. Water consumption is typically 2-5 gallons per hour.

Second Exemplary Bio-Waste Sterilization System

Figure 2:
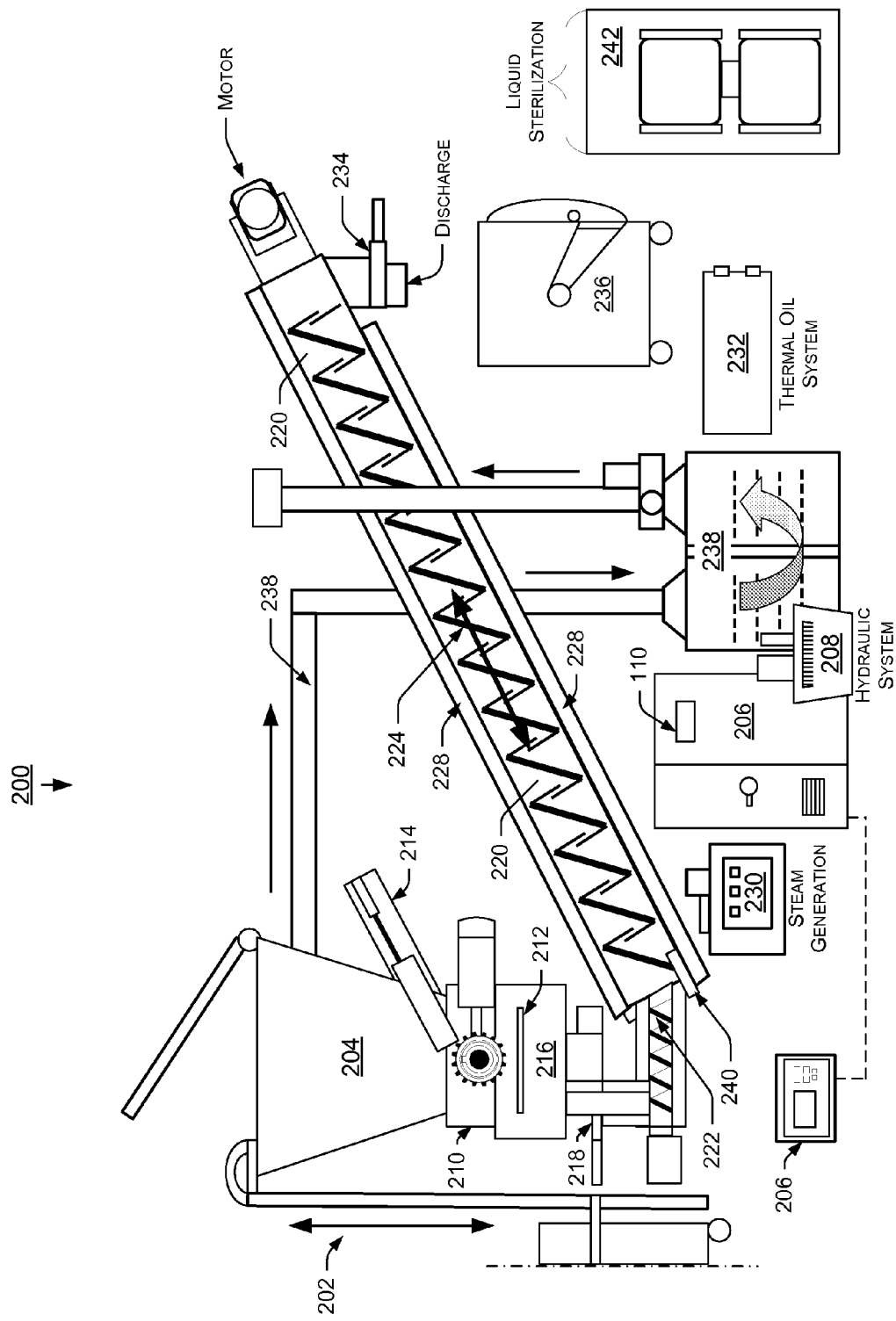
FIG. 2 is diagram of a second exemplary implementation of a bio-waste sterilizer.

FIG. 2 shows another implementation of the exemplary bio-waste sterilizer 200. The waste to be sterilized is placed on the feed system, consisting of a lifting/dumping system 202 and a feed hopper 204. The individual load weight is electronically measured and the data recorded into the system computing device 206, which includes the exemplary controller 110. In some implementations, the computing device 206 is a general purpose computer, while in other implementations the computing device is a programmable logic controller (PLC) or other device that has a processor or microcontroller, memory, and data storage.

In one implementation, the bio-waste sterilizer 200 also incorporates a sniffing device to recognize any nuclear materials or radioactive isotopes and/or a sniffing device to detect a significant concentration of hydrocarbon-based or hydrocarbon contaminated wastes.

In one implementation, the waste is conveyed to the feed hopper 204 by the automatic lifting/dumping system 202, which is powered by a hydraulic pump system 208. The lifting/dumping system 202 may also include a weighing scale. The waste material is passed through a shredder 210 and in one implementation, sized through a grated sieve 212. The feeding process into the shredder 210 can be assisted by a hydraulic ram device 214 mounted, e.g., adjacent to and above the shredder 210 to force oversized or odd-sized waste materials into the cutting mechanism of the shredder 210. The shredded material drops by gravity into a second hopper, e.g., a surge hopper 216 that incorporates a non-clogging dosing feeder.

In one implementation, a first isolation blocking gate valve 218 separates the waste size-reduction/material surge zones (at 212, 216) of the bio-waste sterilizer 200 from a pressure vessel ("treatment vessel" 220) that includes a jacketed charging screw 222 and an exposure/treatment screw 224, these constituting a pressurized treatment/sterilization zone of the bio-waste sterilizer 200. The treatment vessel 220 exposes the waste to heat, provided, for example, by a heating jacket 228, and to steam, provided by a steam generator 230. In one implementation, the heating jacket 228 may contain electric resistance coils or other electric heat-producing components in order to heat parts of the treatment/sterilization zone (e.g., the zone composed of interconnecting cylinders around 222 and 224). In another implementation, the heating jacket 228 uses a flow of hot oil to heat parts of the treatment/sterilization zone. A thermal oil system 232 provides the hot oil and may assist to control its temperature. A second blocking valve 234 (e.g., gate valve) located at the discharge end of the treatment vessel 220 is closed to ensure that no un-sterilized material can exit the bio-waste sterilizer 200 before the sterilization cycle is complete.

The charging screw 222 can convey the shredded waste material into the exposure/treatment screw 224 of the treatment vessel 220. After the exposure/treatment screw 224 has been filled with waste material, the blocking isolation valve 234 is closed, isolating the exposure/treatment screw 224 from the atmosphere and from the untreated waste in the size reduction/material surge zones (at 212, 216).

The controller 110 increases the pressure/temperature combination to a predetermined set point, for example, 140° C./3.1 bar, and maintains the temperature and pressure for a predetermined time, for example, 10 minutes. At the completion of the sterilization process, steam used in the process may be vented back into the bio-waste sterilizer 200 to pre-heat the waste material stored in the surge hopper 216. The isolation valve 234 at the discharge end of the treatment vessel 220 is then opened and the sterilized waste is conveyed into an appropriate waste container 236 for disposal.

Temperature, pressure, and exposure time are adjustable via the controller 110 and can be preset per local regulations. During the sterilization process, the waste can be continually tumbled while conveyed, and thus exposed to sterilization action by the screw motion of the treatment screws 222, 224, ensuring that all of the waste is fully exposed to the steam and heat of the sterilization process.

During the loading process, the entire feed system or feed hopper 204 is held continually under negative air pressure or vacuum by a built-in air filtration system 238. The air being pumped out to create the negative pressure can be processed through a state-of-the-art three-stage air filtration system, which in one implementation includes an activated charcoal stage; an aluminum oxide ceramics stage; and a HEPA filter(s) stage.

As an option, excess liquid is separated via a liquid drain 240 at the feed end of the exposure/treatment screw 224 and pumped to a liquid sterilization system 242. The liquid sterilization system 242 may consists of a storage/holding tank and a sterilization/disinfection pressure vessel. The pressure vessel can be a double-shell design with a heated jacket 228 to accurately control the temperature of the sterilization process. After completion of the liquid sterilization at an appropriate temperature/time process, the steam is vented from the pressure vessel 220 and the sterilized liquid is discharged through piping for appropriate customer disposal.

In one implementation, the above-described bio-waste sterilizer 200 has a waste treatment rate of approximately 1100 pounds per hour, when the bulk weight of the waste is approximately 8 pounds per cubic foot. The volume of the feed hopper 204 is approximately 50 cubic feet or more. The shredder 210 is powered by a motor that may be approximately 30 horsepower. In this implementation, the heating jacket 228 around the treatment screws (e.g., 224) preferably uses heated oil to accomplish heat transfer between a separate thermal oil system 232 and the waste. The oil is electrically heated at the thermal oil system 232 and circulated from the thermal oil system 232 to the heating jacket 228 and back. The thermal oil-mediated electric heating provides a waste preheating output of approximately 20-40 kW. The waste treatment temperature is approximately 284° Fahrenheit. The steam set-output is approximately 72 kW. For the air filtration system 126, a 5 horsepower blower motor may be used to implement a negative air pressure at the feed hopper 204 and HEPA filtration of air drawn from the feed hopper 204 at a rate of approximately 2300 cubic feet per minute. In one implementation, the bio-waste sterilizer is connected to a 440 volt, 60 hertz, 3-phase power source and consumes approximately between 250 kW. Water consumption is typically 25 gallons per hour.

Exemplary Controller

The sterilization, safety, and communication processes for the exemplary bio-waste sterilizer 100 & 200 are administrated, monitored, diagnosed, recorded, etc., by the exemplary controller 110.

Figure 3:
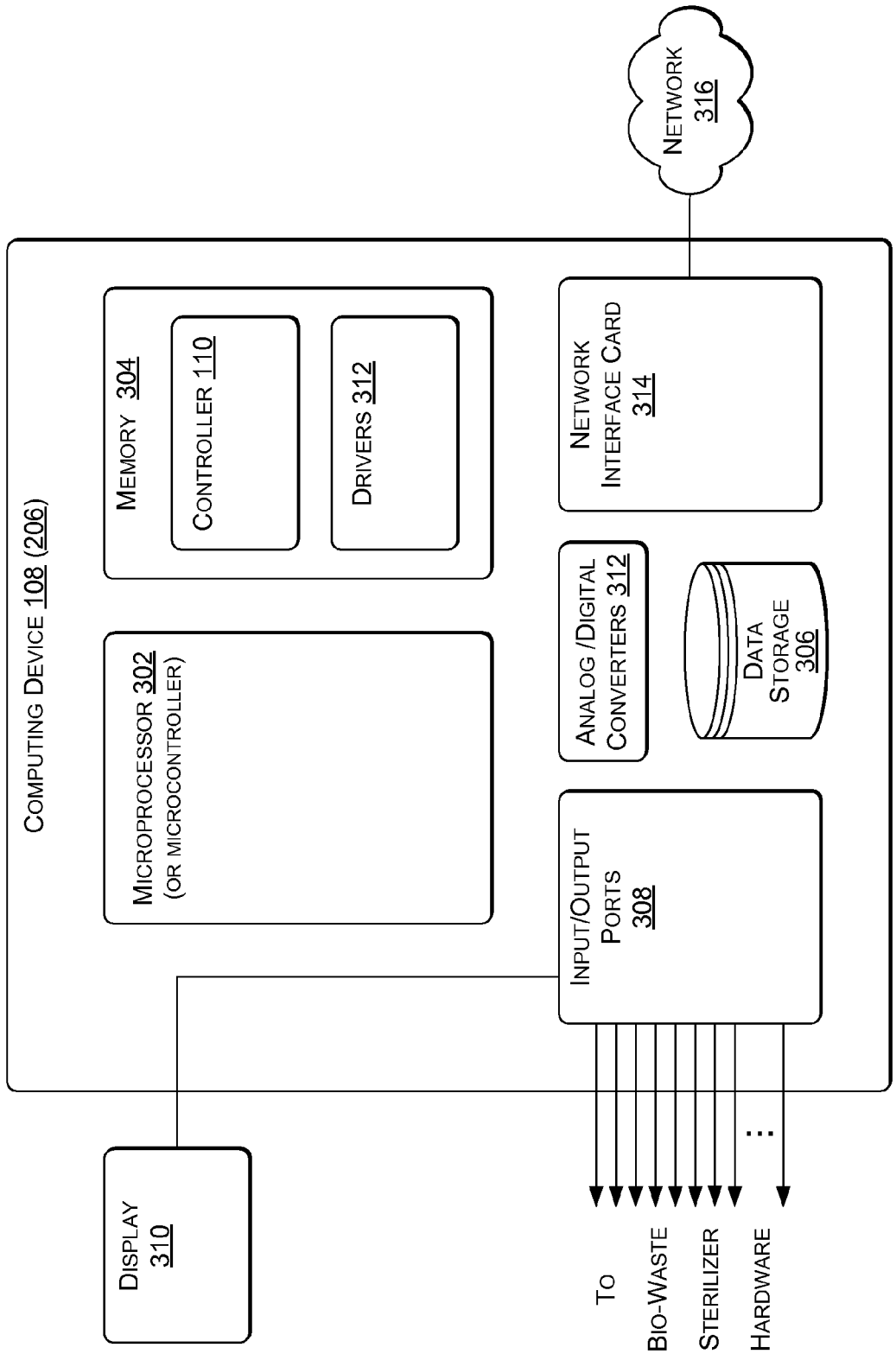
FIG. 3 is a block diagram of an exemplary computing device component of the bio-waste sterilizer, providing an environment for an exemplary controller.

FIG. 3 shows the exemplary computing devices 108 & 206 of FIGS. 1 and 2, in greater detail. The illustrated computing device 108 & 206 is just one example implementation, for the sake of description. Other configurations of hardware and software, including processor, memory, data storage, and the controller 110 can also be used to control and operate the bio-waste sterilizer 100 & 200.

In FIG. 3, the exemplary computing device 108 & 206 includes at least a microprocessor 302 (or a microcontroller), memory 304, data storage 306, input/output ports 308, and a network interface card 310. The computing device 108 & 206 can be a general purpose computer, or can be a programmable logic controller (PLC), depending on implementation. The input/output ports 308 are communicatively coupled with the hardware of the bio-waste sterilizer 100 & 200, that is, to monitoring sensors, probes, and switches, etc., that gather information about the current waste material being processed; the status of the mechanical devices of the bio-waste sterilizer 100 & 200; and the physical conditions inside and outside the bio-waste sterilizer 100 & 200. Analog/digital converters 312 may convert analog sensor signals to digital data as needed.

The input/output ports 308 are also communicatively coupled with actuating devices of the bio-waste sterilizer 100 & 200, i.e., the display 314 and alarms that provide visual and audio readout; the switches, sensors, relays, circuits, etc., that run the hardware of the bio-waste sterilizer 100 & 200, such as motors, solenoids, valves, heating elements, etc. Such control is described more fully below in the description of the controller 110.

In one implementation, many of the components of the exemplary controller 110 are software, which reside in the memory 304 and can be loaded from the data storage 306. Software drivers 316 for the various hardware components that are coupled with the input/output ports 308 may also reside in memory 304. The network interface card (NIC) 310 enables communication of data, signals, statuses, messages, statistics, and records over a network 318, such as the Internet.

Figure 4:
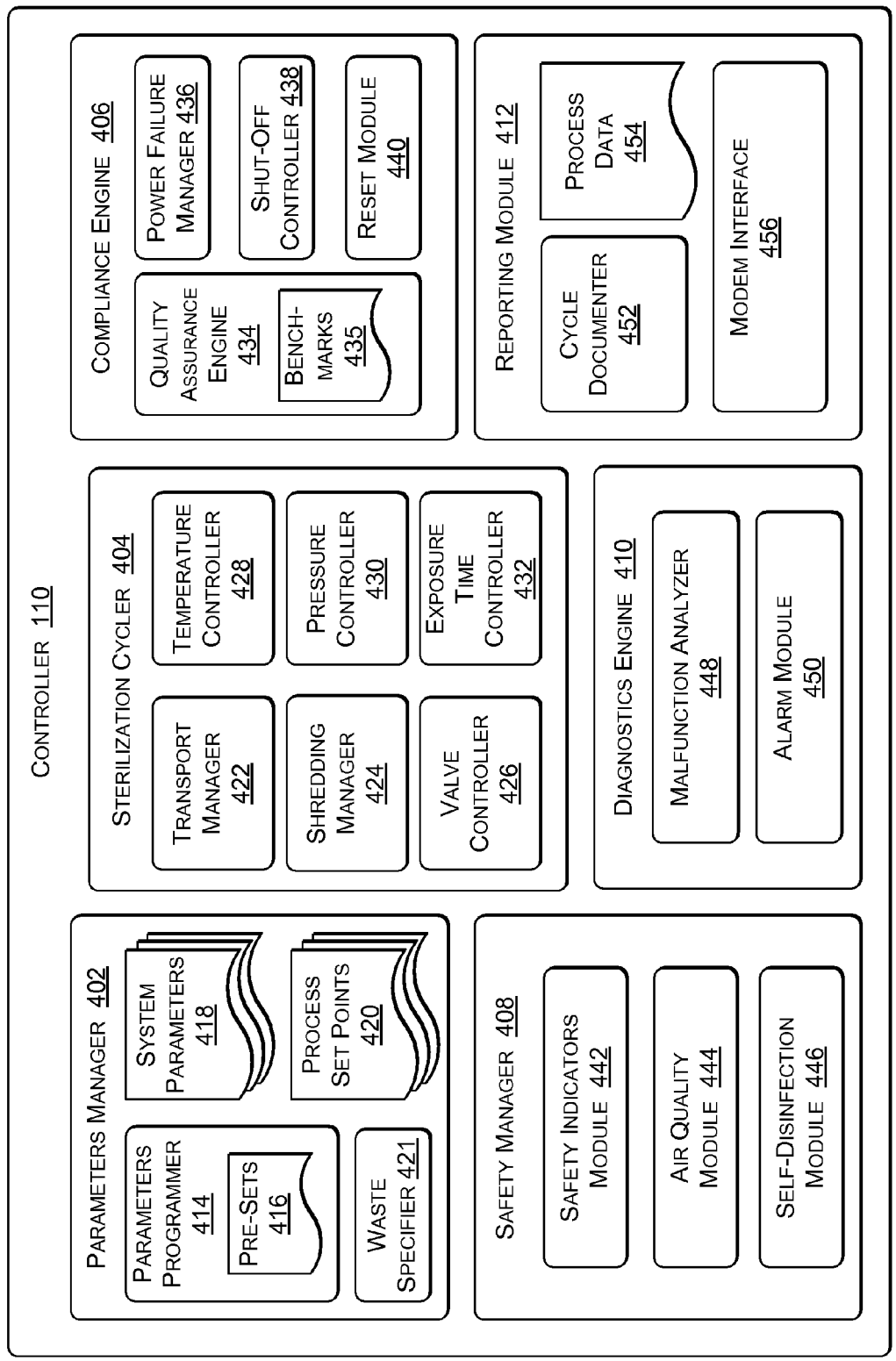
FIG. 4 is a block diagram of the exemplary controller of FIGS. 1-3, in greater detail.

FIG. 4 shows an exemplary implementation of the controller 110 shown in FIGS. 1-3, in greater detail. The illustrated example controller 110 possesses a certain configuration of components for the sake of description. Other arrangements of the same or like components can also be used in other implementations of the controller 110. The controller 110 can be implemented in hardware and software; e.g., as software running on a computing device 108 & 206, such as a general purpose computer or a programmable logic controller (PLC) system; or as software or firmware committed to hardware in an application specific integrated circuit (ASIC) or the like.

The illustrated controller 110 includes a parameters manager 402, a sterilization cycler 404, a compliance engine 406, a safety manager 408, a diagnostics engine 410, and a reporting module 412. The parameters manager 402 may further include a parameters programmer 414, which has access to "pre-sets" 416, i.e., pre-determined values of system parameters 418 and process set points 420. The set points 420 are the values, e.g., for time, temperature, pressure, steam concentration, needed to effect sterilization, and/or the amount of sterilization exposure that waste should have by the time the waste reaches certain waypoints along a waste transport route or sterilization pathway in the bio-waste sterilizer 100 & 200 (quantified in case of shut-down or breakdown). The former may be determined by local regulations. The system parameters 418 and process set points 420 are translated into machine operations at the sterilization cycler 404 to accomplish the point goals or benchmarks 435.

In one implementation, a waste specifier 421 allows a humqn user or operator to specify the type of waste. The waste may be categorized by degree of contamination (e.g., heavy, average, light); or by character (high sharps content, high organic content; mixed, etc.); or by liquid content (e.g., mostly liquids, partially liquids, little or no liquids), and so forth. The sterilization cycler 404 contains logic to modify the sterilization operations to apply the optimal sterilization techniques or best combination of sterilization agents to the type of waste. In other words, if the waste has a high liquid content, then the sterilization cycler 405 may activate the liquid drain 240 and the liquid sterilizer 242—that is, the bio-waste sterilizer 100 & 200 has the capacity to behave differently depending on variations in the type of waste.

The sterilization cycler 404 operates the communicatively coupled equipment to effect sterilization according to the system parameters 418 and process set points 420. In one implementation, the sterilization cycler 404 may include a transport manager 422 to monitor and implement movement of the waste through the bio-waste sterilizer 100 & 200. The transport manager 422 may also control how many times the waste being transported is recycled though a loop of the machine, such as a loop of repeated shredding operations, e.g., through the treatment screws 114, 116, 118, and the shredder 112. The transport manager 422 may also control the reversal of the blade motion of a treatment screw 118, such as for diverting a usual transport path of the waste to a discharge opening on a sterilization pathway.

Likewise, a shredding manager 424 in the sterilization cycler 404 controls the shredding operation, which may include transport of the waste near the shredder itself 112 & 210; and the speed, cutting parameters, and shred size when an adjustable shredder 210 is used.

The sterilization cycler 404 also includes a valve controller 426, which may also track an open/close state of a lid or door of the feed hoppers 102 & 204, in addition to the valves per se.

The valve controller 426 implements isolation of waste from the environment during sterilization, by shutting the blocking valves, such as valves 122, 218, 234. The valve controller 426 may also control functions such as steam generation and flow, contaminated liquid transport in relation to the liquid sterilizer 242, and flow of heated oil to the heating jacket 228, etc. The valve controller 426 can manage, e.g., via solenoids, pneumatic valves, hydraulic valves, fluid valves, to control the flows of solid waste, liquid waste, water, steam, air, hydraulic fluid, thermal oil, etc., in addition to controlling the valves 122, 218, 234 that seal off the treatment vessel 120 & 220 during a sterilization cycle.

The sterilization cycler 404 includes a temperature controller 428, a pressure controller 430, and an exposure time controller 432 to execute sterilization set points 420, e.g., a certain temperature at a certain pressure for a certain duration of time. Each of these components receives input from associated sensors placed in relevant locations of the bio-waste sterilizer 100 & 200. Likewise, each of these components (428, 430, 432) passes instructions to the transport manager 422, shredding manager 424, and valve controller 426, and to other management functions built into the fabric of the sterilization cycler 404 and controller 110.

The sterilization cycler 404 monitors the various physical properties of the bio-waste sterilizer, such as internal temperature and pressure, oil temperature in the heating jacket 228, airflow, location, weight, volume, density, and transport characteristics of the waste; screw positions, valve positions, door positions, container presence, motor speeds, input voltage and water pressure, via various sensors placed in relevant locations of the bio-waste sterilizer 100 & 200. Analog to digital converters process signal input from the sensors as needed. The sensors may include temperature probes suitable for high temperature thermometry, pressure and vacuum sensors and switches, microswitches, limit switches, position sensors and switches, tachometers, optical sensors, electronic weight scales, voltage and current sensors, etc.

The compliance engine 406 may include a quality assurance engine 434, a power failure manager 436, a shut-off controller 438, and a reset module 440. The quality assurance engine 434 receives data that is input from sensors to calculate and to verify whether sterilization benchmarks 435 have been met.

The safety manager 408 may further include a safety indicators module 442 to manage the various safety issues and physical indicators (lights, alarms, buzzers, messages) associated with: hot steam under pressure, hot oil, thermally hot machine zones, contamination cautions, malfunction warnings, safety status indicators, etc. The safety manager 408 includes an air quality module 444 to monitor and manage air being withdrawn from the feed system (such as from the feed hopper 102 & 204 in order to effect a partial vacuum to keep contaminants from escaping the bio-waste sterilizer 100 & 200 via airborne means prior to their sterilization). A self-disinfection module 446 self-sterilizes the bio-waste sterilizer 100 & 200 prior to allowing the interior or treatment vessel zones of the bio-waste sterilizer 100 & 200 to be accessed by maintenance personnel.

The diagnostics engine 410 may further include a malfunction analyzer 448 and an alarm module 450. Upon detection of a failure or deviation in normal operational functions, the malfunction analyzer 448 may proceed down a tree of troubleshooting logic to determine or estimate a problem and its likely cause. In some cases the diagnostics engine 410 can apply its own remedial action to the bio-waste sterilizer 100 & 200 (e.g., extend time duration of waste exposure to pressurized steam) or may initiate an alarm via the alarm module 450 or send a signal for maintenance.

The reporting module 412 may further include a cycle documenter 452 that records the operations, process data 454, and histories of each sterilization cycle. The process data 454 may include a success summary of a sterilization operation, parameters used, and in some cases statistics, comparisons, and a verification that sterilization has been effectuated. In one scenario, the cycle documenter 452 and the bio-waste sterilizer 100 & 200 itself may be approved by a standards body to issue a digital or paper certificate of adequate sanitation, decontamination, and/or sterilization of a given lot of waste material. The process data 454 as well as any current status of the bio-waste sterilizer 100 & 200 or the current load of waste may be transmitted locally or remotely, e.g., over a network or phone service in real time, or as data that has been stored (306) and retrieved.

In one implementation, the controller 110 is programmed into a programmable logic controller system (PLC). The PLC may utilize color display (SPS/OP from SIEMENS or another similar system). A PLC is typically a digital computer used for automation of industrial processes, such as control of machinery on factory assembly lines. Unlike general-purpose computers, the PLC is designed for multiple input and output arrangements, extended temperature ranges, immunity to electrical noise, and resistance to vibration and impact. Programs to control machine operation are typically stored in battery-backed or non-volatile memory.

The main difference from other computers is that PLCs are armored for severe conditions (dust, moisture, heat, cold, etc.) and have the facility for extensive input/output (I/O) arrangements. These connect the PLC to the sensors and actuators of the bio-waste sterilizer 100 & 200. When the controller 110 is implemented in a PLC, the implemented controller 110 can read limit switches, analog process variables (such as temperature and pressure), and the positions of simple or complex positioning systems. In one implementation, the controller 110 may use machine vision to ascertain waste properties and transport statuses. On the actuator side, the PLC-implemented controller 110 can operate electric motors, pneumatic and hydraulic cylinders, magnetic relays, solenoids, and other analog devices. The input/output arrangements may be built into a simple PLC, or the PLC may have external I/O modules attached to a computer network that plugs into the PLC.

Included in such a control system is the capacity for handling information, including system parameters 418, temperature data, time data, data for set points 420, safety indicators 442, remote reporting 412, and diagnostics 410. A malfunction, for example, is indicated on the display 310 and may be further broadcast by an audible alarm 450. The sterilization process is documented 452 and process data 454 may be stored in the onboard computer module 108 or 206. The data can be recalled or printed out at any time during and after operation.

Upon power failure or other non-compliance with the set point parameters 420, the bio-waste sterilizer 100 & 200 automatically shuts off 438 such that no "untreated" waste can be released to the environment. When the bio-waste sterilizer 100 & 200 is then re-started, the controller 110 automatically re-sets 440 to the set points 420 in a time-controlled fashion to provide safe treatment of the waste.

The safety manager 408 acts such that in the event of any routine maintenance or repair work, the self-disinfection module 446 subjects all "impure" areas of the bio-waste sterilizer 100 & 200 to an automatic, thermal self-disinfection process, using raw steam applied over a pre-set time period, prior to any exposure of the potentially contaminated parts of the bio-waste sterilizer 100 & 200 to maintenance personnel.

Figure 5:
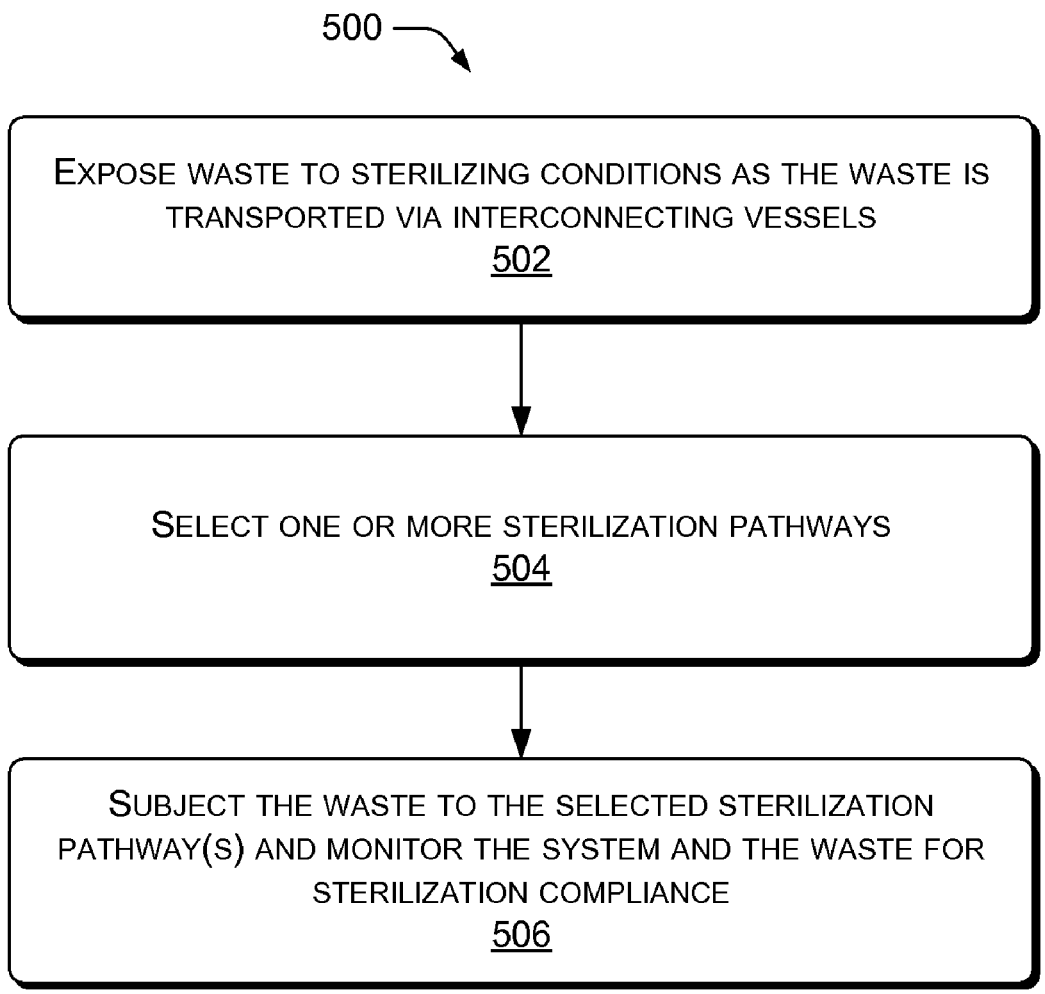
FIG. 5 is a flow diagram of an exemplary method of bio-waste sterilization.

FIG. 5 shows an exemplary method 500 of sterilizing bio-waste via an exemplary bio-waste sterilizer. In the flow diagram, the operations are summarized in individual blocks. The exemplary method 500 may be performed by hardware and software, for example, by components of the exemplary bio-waste sterilizer 100 & 200 and/or by the exemplary controller 110.

At block 502, waste is exposed to sterilizing conditions as the waste is transported via interconnecting vessels. The vessels can be intermittently heated and pressurized (e.g., to enable loading the waste), e.g., by steam and/or by heating jackets that contain electric resistance coils or a flow of thermally heated oil.

At block 504, one or more sterilization pathways are selected by a controller or by a human operator. The sterilization pathways can be physical transport options, such as sending the waste through an agitation cycle while exposing the waste to heat and pressure; recycling the waste multiple times through an increasingly stringent shredder; sending the waste through a liquid separation cycle to draw off aqueous and organic liquids for separate sterilization; sending the waste through various steam, heat, pressure zones; and sending the waste for safe discharge, etc. The sterilization pathways can also be physical treatment options, such as time of exposure needed to sterilize at given temperature, steam, and pressure concentrations, or with a given amount of tumbling during transport; or at a given shred size imposed on the waste. Various segments or zones of an exemplary bio-waste sterilizer system may be selected to best provide the features of each selected sterilization pathway.

At block 506, the waste is subjected to the selected sterilization pathway(s) and both the system and the waste are monitored for sterilization compliance.

Conclusion

Although exemplary systems have been described in language specific to structural features and/or methodological acts, it is to be understood that the subject matter defined in the appended claims is not necessarily limited to the specific features or acts described. Rather, the specific features and acts are disclosed as exemplary forms of implementing the claimed systems, methods, and structures.

The invention claimed is:

1. A system, comprising:
   a first vessel for holding waste material;
   a second vessel that includes a first screw conveyor for transporting a flow of the waste material from the first vessel;
   a third vessel for receiving the flow of the waste material from the second vessel, the third vessel including a second screw conveyor for transporting the flow of the waste material through sterilization conditions;
   a controller to monitor the sterilization conditions and safety conditions of the system and to operate components of the system;
   a compliance engine to monitor the sterilization conditions and compare an exposure of the waste material to the sterilization conditions against a sterilization benchmark to ensure a quality of the sterilization;
   a power failure manager to ensure a sterilization cycle is complete in the event of a power failure in which power fails to be provided to the system;
   a shut-off controller to cease operation of the system in the event of a malfunction; and a reset module to reinitiate an operation of the system from set points or from way points during the sterilization cycle.

2. The system as recited in claim 1, wherein the controller includes a parameters manager to enable selection of sterilization set points, including temperatures;
an associated pressure for each temperature;
a time of exposure for each temperature and pressure combination; and
wherein each temperature, pressure, and time of exposure combination is sufficient to sterilize the waste material.

3. The system as recited in claim 2, wherein the controller further comprises a waste specifier; and
wherein the controller matches a temperature, pressure, and time of exposure combination to a specified type of waste based on attributes of the type of waste.

4. The system as recited in claim 1, wherein the controller includes a sterilization cycler, further including:
a transport manager;
a shredding manager;
a valve controller;
a temperature controller;
a pressure controller; and
an exposure time controller.

5. The system as recited in claim 4, wherein the transport manager controls a speed of transport of the waste material to ensure sterilization of the waste material given the sterilization conditions.

6. The system as recited in claim 4, wherein the transport manager selects a number of transport cycles for the waste material to cycle through the system to ensure sterilization of the waste material given the sterilization conditions.

7. The system as recited in claim 4, wherein the transport manager cycles the waste material through a shredder multiple times; and
wherein the shredding manager shreds the waste material to a smaller shred size with each cycle.

8. The system as recited in claim 7, wherein the transport manager adjusts a speed of transport in real time in proportion to current sterilization conditions; and
wherein the sterilization conditions include:
a current temperature in the system;
a current pressure in the system;
an elapsed time of exposure of the waste material to the sterilization conditions; and
a current shred size of the waste material indicative of a surface area of the waste material being exposed to the sterilization conditions.

9. The system as recited in claim 1, wherein the controller further comprises a safety manager, including:
a safety indicator module to control safety indicators and alarms;
an air quality module to monitor air removed from the system and air filtered to provide a negative pressure in at least a part of the system; and
a self-disinfection module to self-sterilize the system before access to an interior of the system by maintenance personnel.

10. The system as recited in claim 1, wherein the controller further comprises a diagnostics engine to analyze malfunctions and signal an alarm module, and automatically apply troubleshooting and repair measures or call for maintenance.

11. The system as recited in claim 1, wherein the controller further comprises:
an information reporting module to document sterilization cycles, system parameters, compliance data, process data, and statistics about an operation of the system; and
a network interface or modem interface for transmitting the information.

* * * * *